(12) United States Patent
Singer

(10) Patent No.: US 6,587,715 B2
(45) Date of Patent: Jul. 1, 2003

(54) ASSESSMENT OF ORGANS FOR TRANSPLANT, XENOTRANSPLANT, AND PREDICTING TIME OF DEATH

(75) Inventor: Michaeal G. Singer, Harrisville, MI (US)

(73) Assignee: The Nutrition Solutions Corporation, Harrisville, MI (US)

( * ) Notice: Subject to any disclaimer, the term of this patent is extended or adjusted under 35 U.S.C. 154(b) by 159 days.

(21) Appl. No.: 09/848,242

(22) Filed: May 3, 2001

(65) Prior Publication Data

US 2002/0165464 A1 Nov. 7, 2002

(51) Int. Cl.$^7$ ................................................ A61B 5/04
(52) U.S. Cl. ........................ 600/547; 600/386; 128/898
(58) Field of Search .............................. 600/300, 384, 600/506, 546, 547, 508, 536, 587; 324/76.41, 89, 611, 668, 670, 692; 330/51, 69; 128/898

(56) References Cited

U.S. PATENT DOCUMENTS

| | | | | | |
|---|---|---|---|---|---|
| 3,971,366 A | * | 7/1976 | Motoyama | .................. | 600/384 |
| 4,008,712 A | * | 2/1977 | Nyboer | ........................ | 600/547 |
| 4,557,271 A | * | 12/1985 | Stoller et al. | ................ | 600/547 |
| 4,911,175 A | * | 3/1990 | Shizgal | ........................ | 600/547 |
| 5,335,667 A | * | 8/1994 | Cha et al. | .................... | 600/547 |
| 6,024,698 A | * | 2/2000 | Brasile | ........................ | 600/300 |
| 2002/0123694 A1 | * | 9/2002 | Organ et al. | ................. | 600/547 |

* cited by examiner

Primary Examiner—Tu Ba Hoang
(74) Attorney, Agent, or Firm—Irving M. Weiner; Pamela S. Burt; Weiner & Burt, P.C.

(57) ABSTRACT

A method for determining illness, progression to death, and timing of death of a biological entity, in which whole body measurements of electrical impedance and composition of the biological entity are taken and recorded at predetermined intervals of time for providing initially measured values and serially measured values, and then the initially measured values are compared to normal values and to the serially measured values to determine hallmarks or characteristics of illness, progression to death and timing to death of the biological entity.

17 Claims, No Drawings

ASSESSMENT OF ORGANS FOR TRANSPLANT, XENOTRANSPLANT, AND PREDICTING TIME OF DEATH

This document may contain material which is the subject of copyright protection. All rights in such copyrightable material are hereby reserved.

The present invention relates generally to a method and system for utilization of bioelectrical impedance analysis (BIA) in a biological model for body composition analysis (BCA) to provide an objective assessment of an organ's and/or biological entity's volume and distribution of fluids and tissue as well as the electrical health of cells and membranes.

More particularly, the present invention relates to a method for determining illness of a biological entity, progression to death of said biological entity, and/or timing of death of said biological entity, and also relates to a method of organ vitality assessment for transplantation of said organ being assessed.

BACKGROUND OF THE INVENTION

The relevant art is exemplified by the following U.S. patents.

U.S. Pat. No. 2,111,135 issued in 1938 to Bagno entitled "APPARATUS AND METHOD FOR DETERMINING IMPEDANCE ANGLES" discloses an apparatus for measuring the electrical phase displacing properties or impedance angle of humans, animals, and vital tissues. There is also disclosed a method for measuring the phase angle due to the impedance of an animal having properties of varying resistance and capacitance due to changes in muscular tension, comprising the steps of passing an alternating current through the animal, and measuring the phase during changes of resistance and capacitance, said measurement of phase being made so that the phase angle remains substantially independent of variations in the total impedance.

U.S. Pat. No. 2,852,739 issued in 1958 to Hansen entitled "REMOTE CONTROLLED IMPEDANCE MEASURING CIRCUIT" discloses a remotely controlled measuring circuit for a monitoring apparatus of the type which provides an indication of the change in electrical impedance in a sensing element brought about by some change in the physical or chemical characteristics of an object being monitored.

U.S. Pat. No. 3,085,566 issued in 1963 to Tolles entitled "APPARATUS FOR MEASURING THE ELECTRICAL RESPONSE OF LIVING TISSUE" discloses an apparatus for measuring tissue resistance and capacitance independently of tissue potential. While particularly useful in measurements on living tissue, the invention may also be used to measure electrical effects as the tissue dies.

U.S. Pat. No. 3,316,896 issued in 1967 to Thomasset entitled "APPARATUS AND METHODS FOR THE MEASURE OF THE ELECTRICAL IMPEDANCE OF LIVING ORGANISMS" discloses a method for simultaneously and associatively determining the individual impedances of the extracellular contents and the intracellular contents of a living organism, which consists in measuring the total impedance of the organism between two selected points thereof at predetermined frequencies.

U.S. Pat. No. 3,498,288 issued in 1970 to Max et al. entitled "DEVICE FOR CORRECTING THE MEASUREMENT OF POTENTIALS DETECTED BY CONTACT ELECTRODES" discloses a device for rapidly correcting the measurement, supplied by an apparatus comprising a continuously operating metering amplifier, of the potential detected in an organ of the human body by means of two contact electrodes. The device includes means for resetting the zero of the metering amplifier, and means for compensating the polarization voltage of the contact electrodes in use.

U.S. Pat. No. 3,882,851 issued in 1975 to Sigworth entitled "IMPEDANCE PLETHYSMOGRAPH" discloses a device provided with voltage and current electrodes with a variable current source connected to the current electrodes to send a varying current to a biological segment to provide a voltage that is used to generate a signal representing a percent of change in the resistance of the biological segment.

U.S. Pat. No. 4,823,804 issued in 1989 to Ghislaine et al. entitled "APPARATUS FOR MONITORING ACTIVITY LEVEL OF HUMAN ORGAN" discloses an apparatus for monitoring the motricity of an organ by a counterreaction technique known as bioretroaction. The apparatus has at least one pair of differential-connected sensors placed near the organ for obtaining differential electric input signals representing the activity of the organ. A computer processes the input signals to generate an output signal which is characteristic of the activity level of the organ.

U.S. Pat. No. 5,372,141 issued in 1994 to Gallup et al. entitled "BODY COMPOSITION ANALYZER" discloses a body composition analyzer which provides the resistive and reactive components of a body's measured impedance as well as body fat information and ideal weight information.

U.S. Pat. No. 6,024,698 issued in 2000 to Brasile entitled "APPARATUS FOR MONITORING FUNCTIONAL CHARACTERISTICS OF AN ORGAN INTENDED FOR TRANSPLANTATIONS" discloses a technique to prospectively determine the potential function of an organ posttransplantation by measuring functional characteristics related to organ metabolism while the organ is being perfused in an ex vivo warm preservation system at near normal rate of metabolism by measuring parameters of organ product or circulated perfusate during ex vivo preservation. Values of the measured parameters are compared to reference interval values (an established normal range) so that a value of a measured parameter outside the reference intervals may indicate organ damage, injury, or poor functional capabilities that may affect the function of the organ posttransplantation.

The desiderata of the present invention are to avoid the animadversions of conventional methods and techniques, and to provide a novel method for determining illness of a biological entity, progression to death of said biological entity, and/or timing of death of said biological entity, and to provide a novel method of organ vitality assessment for transplantation and/or xenotransplantation of said organ being assessed.

SUMMARY OF THE INVENTION

The present invention provides a method for determining illness of a biological entity, progression to death of said biological entity, and/or timing of death of said biological entity, comprising the steps of: providing normal values of resistance, reactance, phase angle, extracellular water volume, and intracellular water volume of the whole body of the biological entity; measuring initial values of resistance, reactance, phase angle, extracellular water volume, and intracellular water volume of the whole body of the biological entity; taking whole body measurements of resistance, reactance, phase angle, extracellular water volume, and intracellular water volume at predetermined intervals of time; recording said whole body measurements; comparing initial values of said whole body measurements to normal values of said whole body measurements and to serially measure values of said whole body measurements; and determining, from said comparison step, hallmarks of said illness of said biological entity, said progression to said death of said biological entity, or said death of said biological entity.

The present invention also provides a method of organ vitality assessment for transplantation of said organ being assessed, comprising the steps of: placing signal introduction electrodes on opposite lateral peripheral borders of said organ upon harvesting of said organ; placing signal detection electrodes at superior and inferior borders of said organ for a first part of an initial measurement upon said harvesting of said organ; measuring and recording first values of resistance and reactance of said organ in said initial measurement; then placing said signal introduction electrodes on said superior and said inferior borders of said organ; placing said signal detection electrodes on said opposite lateral borders of said organ; measuring and recording second values of said resistance and said reactance of said organ; and comparing said first and second values to normal values to determine if said organ is acceptable or not for said transplantation.

DETAILED DESCRIPTION OF THE INVENTION

BIA is an electrodiagnostic methodology based upon the conductive properties of the body's tissues, cells, and fluids. The BIA instrument, such as that disclosed in the aforementioned U.S. Pat. No. 5,372,141, an impedance plethysmograph, may use a constant current source producing a low-voltage electrical signal, usually 800 micro-amps at a high frequency, often fixed at 50 KHz, to set up an electrical field in the whole body or a body segment using two pairs of surface ECG-type electrodes, designated as a Tetra-Polar Electrode Scheme as described by Nyboer in U.S. Pat. No. 4,008,712.

The methods of the present invention can utilize a modification of the body composition analyzer disclosed in U.S. Pat. No. 5,372,141, the entire contents of which are incorporated herein by reference thereto.

In accordance with the present invention, utilization of BIA in a biological model for BCA provides an objective assessment of the study subject's (whole body or organ) volume and distribution of fluids and tissues, as well as the electrical health of the cells and membranes.

The characteristics of BIA include precision, accuracy, feasibility and economy. BIA may be applied to any area of interest, regionally, or to the whole body. It is non-offensive, causing no harm. It may be repeated freely, as desired, to illustrate change over time so that progression of conditions can be monitored and intervention modified.

One aspect of the present invention applies the BIA technology for BCA assessment of vitality of organs for transplant, vitality of organs from other species for human transplantation (xenotransplantation), and to monitor and assess the timing of death.

Organ vitality assessment is based upon the ability of a modified BIA for BCA to illustrate the health of cells by the measured reactance (X).

Upon organ harvest, signal introduction electrodes are placed on the opposite lateral peripheral borders of the organ being assessed, and signal detection electrodes are placed at the superior and inferior borders of the organ being assessed for the first part of the initial measurement.

The values of electrical resistance (R) and impedance (X) are measured and recorded.

The signal introduction electrodes are then re-positioned or placed on the superior and inferior borders of the organ being assessed, while the signal detection electrodes are now re-positioned or placed the opposite lateral peripheral borders of the organ being assessed.

Further values of R and X are measured and recorded.

The values are then compared to normal values, and the organ is determined to be acceptable or not.

If acceptable, prior to organ implant (transplantation or xenotransplantation), the sequence of steps described hereinabove is repeated with comparison being made to the electrical values which were measured and recorded upon organ harvest.

The values should be within an acceptable range of agreement denoting no further loss of organ vitality, and then the implantation is completed.

In accordance with the present invention, the same scenario is utilized for organs from different species.

For determination of the timing of death, whole body measurements are made at predetermined intervals of time (preferably, but not necessarily, every other day) with electrical resistance (R), reactance (X), and phase angle ($\phi$) being measured and recorded. Initial values are compared to normal values and to those serially measured and recorded.

The initial values are defined as those resulting from the first measurement.

The normal values are well known to persons skilled in this particular area of technology, and are cited in various textbooks and patents. For example, note the normal values stated at columns 5 and 6 of U.S. Pat. No. 4,008,712.

Normal resistance ranges are from 300 to 1000 ohms, with variation based upon age and gender, however the patient's value becomes the baseline value from which variations are compared to with increases indicative of less fluid and decreases indicative of more fluid.

Normal phase angle is from 4 to 12 degrees, the average phase angle is 5 to 9 degrees, phase angle decrease is indicative of advancing disease, ineffective treatment or poor prognosis, increasing phase angle is indicative of improving health, effective treatment and a good prognosis. A phase angle less than four indicates serious illness, a phase angle less than two heralds impending death. The rapidity the phase angle changes are indicative of the speed of positive or negative progression of health or disease.

ECW (extracellular water) is 40% of TBW (total body water) with a normal range of +/−5%.

ICW (intracellular water) is 60% of TBW (total body water) with a normal range of +/−5%.

TBW normal values are based upon gender and body type, the formal male is 60% (of weight) as water +/−5%, the normal female 55%+/−5%, the obese of either gender 45%+/−5% and the highly muscled of either gender 70%+/−5%.

Measurement frequency is related to the patient's condition and is proportional to the criticality, seriousness or expectation to change as with other evidence of improvement, worsening or expected results from a treatment intervention. More serious equals more frequent, less serious equals less frequent. Generally measurements are made daily or every other day for serious and weekly or monthly for stable or chronic conditions.

The uncorrectable loss of cell mass and membrane capacity, as evidenced by a reduction in X and $\phi$, are by an uncorrectable and increasing disparity of ECW (extracellular water) volume being greater than ICW (intracellular water) volume and remaining uncorrectable, are the hallmarks of the progression to death of the biological entity.

φ values less than four degrees denote serious illness.

φ values less than two degrees denote imminent demise.

One embodiment of the present invention provides a method for determining illness of a biological entity, progression to death of said biological entity, and/or timing of death of said biological entity, comprising the steps of: providing normal values of resistance, reactance, phase angle, extracellular water volume, and intracellular water volume of the whole body of the biological entity; measuring initial values of reactance, phase angle, extracellular water volume, and intracellular water volume of the whole body of the biological entity; taking whole body measurements of resistance, reactance, phase angle, extracellular water volume, and intracellular water volume at predetermined intervals of time; recording said whole body measurements; comparing initial values of said whole body measurements to normal values of said whole body measurements and to serially measured values of said whole body measurements; and determining from said comparison step hallmarks of said illness of said biological entity, said progression to said death of said biological entity, and/or said death of said biological entity.

Another embodiment of the present invention provides a method of organ vitality assessment for transplantation of said organ being assessed, comprising the steps of: placing signal introduction electrodes on opposite lateral peripheral borders of said organ upon harvesting of said organ; placing signal detection electrodes at superior and inferior borders of said organ for a first part of an initial measurement upon said harvesting of said organ; measuring and recording first values of resistance and reactance of said organ in said initial measurement; then placing said signal introduction electrodes on said superior and said inferior borders of said organ; placing said signal detection electrodes on said opposite lateral borders of said organ; measuring and recording second values of said resistance and said reactance of said organ; and comparing said first and second values to normal values to determine if said organ is acceptable or not for said transplantation.

Although the invention has been described in detail in the foregoing only for the purpose of illustration, it is to be understood that such detail is solely for that purpose and that variations can be made therein by those of ordinary skill in the art without departing from the spirit and scope of the invention as defined by the following claims, including all equivalents thereof.

What is claimed is:

1. A method for determining illness of a biological entity, progression to death of said biological entity, or timing of death of said biological entity, comprising the steps of:
   providing normal values of resistance, reactance, phase angle, extracellular water volume, and intracellular water volume of the whole body of the biological entity;
   measuring initial values of resistance, phase angle, extracellular water volume, and intracellular water volume of the whole body of the biological entity;
   taking whole body measurements of phase angle, extracellular water volume, and intracellular water volume at predetermined intervals of time;
   recording said whole body measurements;
   comparing initial values of said whole body measurements to said normal values of said whole body measurements and to serially measured values of said whole body measurements; and
   determining from said comparison steps hallmarks of said illness of said biological entity, said progression to said death of said biological entity, or said timing of death of said biological entity.

2. A method according to claim 1, wherein:
   said hallmarks include an uncorrectable loss of cell mass and membrane capacity as evidenced by a reduction in said reactance and phase angle.

3. A method according to claim 1, wherein:
   said hallmarks include an uncorrectable and increasing disparity of said extracellular water volume being greater than said intracellular water volume.

4. A method according to claim 2, wherein:
   said hallmarks include an uncorrectable and increasing disparity of said extracellular water volume being greater than said intracellular water volume.

5. A method according to claim 2, wherein:
   when said uncorrectable loss of cell mass and membrane capacity remains uncorrectable, said uncorrectable loss of cell mass and membrane capacity comprise hallmarks of said progression of said death of said biological entity.

6. A method according to claim 4, wherein:
   when said uncorrectable loss of cell mass and membrane capacity remains uncorrectable, said uncorrectable loss of cell mass and membrane capacity comprise hallmarks of said progression to said death of said biological entity.

7. A method according to claim 3, wherein:
   when said uncorrectable and increasing disparity of said extracellular water volume being greater than said intracellular water volume remains uncorrectable, said uncorrectable and increasing disparity of said extracellular water volume comprise hallmarks of said progress to said death of said biological entity.

8. A method according to claim 4, wherein:
   when said uncorrectable and increasing disparity of said extracellular water volume being greater than said intracellular water volume remains uncorrectable, said uncorrectable and increasing disparity of said extracellular water volume comprise hallmarks of said progress to said death of said biological entity.

9. A method according to claim 6, wherein:
   when said uncorrectable and increasing disparity of said extracellular water volume being greater than said intracellular water volume remains uncorrectable, said uncorrectable and increasing disparity of said extracellular water volume comprise hallmarks of said progress to said death of said biological entity.

10. A method according to claim 1, wherein:
    values of said phase angle less than four degrees denote serious illness of said biological entity, and
    values of said phase angle less than two degrees denote imminent death of said biological entity.

11. A method according to claim 2, wherein:
    values of said phase angle less than four degrees denote serious illness of said biological entity; and
    values of said phase angle less than two degrees denote imminent death of said biological entity.

12. A method according to claim 3, wherein:
    values of said phase angle less than four degrees denote serious illness of said biological entity; and values of said phase angle less than two degrees denote imminent death of said biological entity.

13. A method according to claim 4, wherein:

values of said phase angle less than four degrees denote serious illness of said biological entity; and values of said phase angle less than two degrees denote imminent death of said biological entity.

14. A method according to claim 5, wherein:

values of said phase angle less than four degrees denote serious illness of said biological entity; and values of said phase angle less than two degrees denote imminent death of said biological entity.

15. A method according to claim 1, wherein:

said whole body measurements of said resistance, said reactance, said phase angle, said extracellular water volume, and said intracellular water volume are taken every other day.

16. A method according to claim 2, wherein:

said whole body measurements of said resistance, said reactance, said phase angle, said extracellular water volume, and said intracellular water volume are taken every other day.

17. A method according to claim 3, wherein:

said whole body measurements of said resistance, said reactance, said phase angle, said extracellular water volume, and said intracellular water volume are taken every other day.

* * * * *